US009700369B2

(12) United States Patent
Shin et al.

(10) Patent No.: US 9,700,369 B2
(45) Date of Patent: Jul. 11, 2017

(54) SYSTEM FOR ABLATION UTILIZING MULTIPLE ELECTRODES AND METHOD FOR CONTROLLING SAME

(71) Applicants: Starmed Co. LTD, Goyang, Gyeonggi-Do (KR); Kyong-Min Shin, Incheon (KR)

(72) Inventors: Kyong-Min Shin, Incheon (KR); Kyung-Hoon Shin, Gyeonggi-Do (KR); Jun-Hyok Lee, Gyeonggi-Do (KR); Young-Jin Choi, Seoul (KR); Jung-Hyuk Zu, Seoul (KR); Kye-Joo Kim, Incheon (KR)

(73) Assignees: Starmed Co., LTD, Goyang, Gyeonggi-Do (KR); Kyong-Min Shin, Incheon (KR)

( * ) Notice: Subject to any disclaimer, the term of this patent is extended or adjusted under 35 U.S.C. 154(b) by 131 days.

(21) Appl. No.: 14/438,551

(22) PCT Filed: Oct. 2, 2013

(86) PCT No.: PCT/KR2013/008808
§ 371 (c)(1),
(2) Date: Apr. 24, 2015

(87) PCT Pub. No.: WO2014/065518
PCT Pub. Date: May 1, 2014

(65) Prior Publication Data
US 2015/0265333 A1    Sep. 24, 2015

(30) Foreign Application Priority Data

Oct. 25, 2012    (KR) .................. 10-2012-0119133

(51) Int. Cl.
*A61B 18/10*    (2006.01)
*A61B 18/14*    (2006.01)
(Continued)

(52) U.S. Cl.
CPC ............... *A61B 18/14* (2013.01); *A61B 5/01* (2013.01); *A61B 5/053* (2013.01);
(Continued)

(58) Field of Classification Search
CPC ...... A61B 18/1206; A61B 2018/00577; A61B 2018/00648; A61B 2018/00654;
(Continued)

(56) References Cited

U.S. PATENT DOCUMENTS 4,473,075 A     9/1984   Rexroth
5,562,720 A *  10/1996   Stern .................. A61B 18/1206
                                                    606/32
(Continued)

FOREIGN PATENT DOCUMENTS

CN       201879818 U     6/2011
KR       10-0648049      11/2006
(Continued)

OTHER PUBLICATIONS

International Search Report—PCT/KR2013/008808.
(Continued)

*Primary Examiner* — Jaymi Della
(74) *Attorney, Agent, or Firm* — Mintz Levin Cohn Ferris Glovsky and Popeo, P.C.; Peter F. Corless

(57) ABSTRACT

There are provided a system for ablation utilizing multiple electrodes and a method for controlling the system. The system includes: a main amplification unit providing main radio frequency (RF) power by amplifying received power; a sub-amplification unit providing sub-RF power by amplifying received power; a first switching unit transmitting the main RF power provided by the main amplification unit to one of first to third electrodes; a second switching unit transmitting the sub-RF power provided by the sub-amplification unit to one of the first to third electrodes; and a
(Continued)

control unit controlling the first and second switching units to apply the main RF power and the sub-RF power to a pair of respective electrodes previously selected from the first to third electrodes.

9 Claims, 2 Drawing Sheets

(51) Int. Cl.
*A61B 5/01* (2006.01)
*A61B 18/12* (2006.01)
*A61B 5/053* (2006.01)
*A61B 18/16* (2006.01)
*A61B 18/00* (2006.01)
*A61B 90/00* (2016.01)

(52) U.S. Cl.
CPC .......... *A61B 18/1206* (2013.01); *A61B 18/16* (2013.01); *A61B 2018/00577* (2013.01); *A61B 2018/00648* (2013.01); *A61B 2018/00654* (2013.01); *A61B 2018/00678* (2013.01); *A61B 2018/00702* (2013.01); *A61B 2018/00708* (2013.01); *A61B 2018/00779* (2013.01); *A61B 2018/00797* (2013.01); *A61B 2018/00827* (2013.01); *A61B 2018/00875* (2013.01); *A61B 2018/00892* (2013.01); *A61B 2018/00898* (2013.01); *A61B 2018/124* (2013.01); *A61B 2018/1273* (2013.01); *A61B 2018/1467* (2013.01); *A61B 2018/165* (2013.01); *A61B 2090/0818* (2016.02)

(58) Field of Classification Search
CPC  A61B 2018/00678; A61B 2018/00702; A61B 2018/00708; A61B 2018/00797; A61B 2018/00827; A61B 2018/00875; A61B 2018/00892; A61B 2018/124

See application file for complete search history.

(56) References Cited

U.S. PATENT DOCUMENTS

| 5,928,159 | A  | * | 7/1999  | Eggers  | A61B 5/0531 600/373 |
|---|---|---|---|---|---|
| 6,039,731 | A  | * | 3/2000  | Taylor  | A61B 5/0422 600/374 |
| 6,514,248 | B1 | * | 2/2003  | Eggers  | A61B 18/1492 606/41 |
| 2003/0195501 | A1 | * | 10/2003 | Sherman | A61B 18/1206 606/34 |
| 2004/0106917 | A1 | * | 6/2004  | Ormsby  | A61B 18/1492 606/33 |
| 2005/0010206 | A1 |   | 1/2005  | Nasab et al. | |
| 2007/0255269 | A1 | * | 11/2007 | Shin    | A61B 18/1206 606/34 |
| 2011/0160716 | A1 |   | 6/2011  | Govari et al. | |

FOREIGN PATENT DOCUMENTS

| WO | 97/33526 A2 | 9/1997 |
| WO | 99/56644 A1 | 11/1999 |
| WO | 01/28455 A1 | 4/2001 |
| WO | 2005/110263 A2 | 11/2005 |

OTHER PUBLICATIONS

English Language Summary of First Office Action issued in corresponding Chinese Application No. 201380056037.X, Dispatch Date: Sep. 23, 2016 (8 Pages).

* cited by examiner

SYSTEM FOR ABLATION UTILIZING MULTIPLE ELECTRODES AND METHOD FOR CONTROLLING SAME

CROSS-REFERENCE TO RELATED APPLICATIONS

This application is a National Phase application filed under 35 USC 371 of PCT International Application PCT/KR2013/008808 with an International Filing Date of Oct. 2, 2013, which claims under 35 U.S.C. §119(a) the benefit of Korean Application No. 10-2012-0119133, filed Oct. 25, 2012, the entire contents of which are incorporated herein by reference.

TECHNICAL FIELD

The present disclosure relates to a system for ablation, and more particularly, to a system for ablation utilizing multiple electrodes and a method for controlling the system.

BACKGROUND ART

Ablation systems are used to treat diseases such as cancer by forming an ablation volume in human tissue. To this end, ablation systems use one or more electrodes to apply radio frequency (RF) power to the body and thus to form an ablation volume in the body.

DISCLOSURE

Technical Problem

In the related art, there is a need for a method of efficiently controlling radio frequency (RF) power applied through multiple electrodes of an ablation system.

Technical Solution

According to an aspect of the present disclosure, a system for ablation may include: a main amplification unit providing main radio frequency (RF) power by amplifying received power; a sub-amplification unit providing sub-RF power by amplifying received power; a first switching unit transmitting the main RF power provided by the main amplification unit to one of first to third electrodes; a second switching unit transmitting the sub-RF power provided by the sub-amplification unit to one of the first to third electrodes; and a control unit controlling the first and second switching units to apply the main RF power and the sub-RF power to a pair of respective electrodes previously selected from the first to third electrodes.

According to another aspect of the present disclosure, a method for controlling a system for ablation utilizing multiple electrodes may include: switching a plurality of electrodes to apply main RF power and sub-RF power to a first pair of electrodes previously selected from the plurality of electrodes; monitoring a voltage and a current of a side to which the main RF power and the sub-RF power are applied for a predetermined period of time; switching the plurality of electrodes to apply the main RF power and the sub-RF power to a second pair of electrodes previously selected from the plurality of electrodes; monitoring a voltage and a current of a side to which the main RF power and the sub-RF power are applied for a predetermined period of time; switching the plurality of electrodes to apply the main RF power and the sub-RF power to a third pair of electrodes previously selected from the plurality of electrodes; calculating a degree of impedance of tissue using monitored voltage and current values; and comparing the calculated degree of impedance with a preset reference value for increasing or decreasing the main RF power and the sub-RF power.

The above-described aspects of the present disclosure do not include all aspects or features of the present disclosure. Other aspects or features, advantages, and effects of the present disclosure will be clearly understood from the following descriptions of exemplary embodiments.

Advantageous Effects

The present disclosure may provide a system for ablation that utilizes multiple electrodes and efficiently controls radio frequency (RF) power applied through the multiple electrodes, and a method for controlling the system.

BEST MODE

Figure 1:
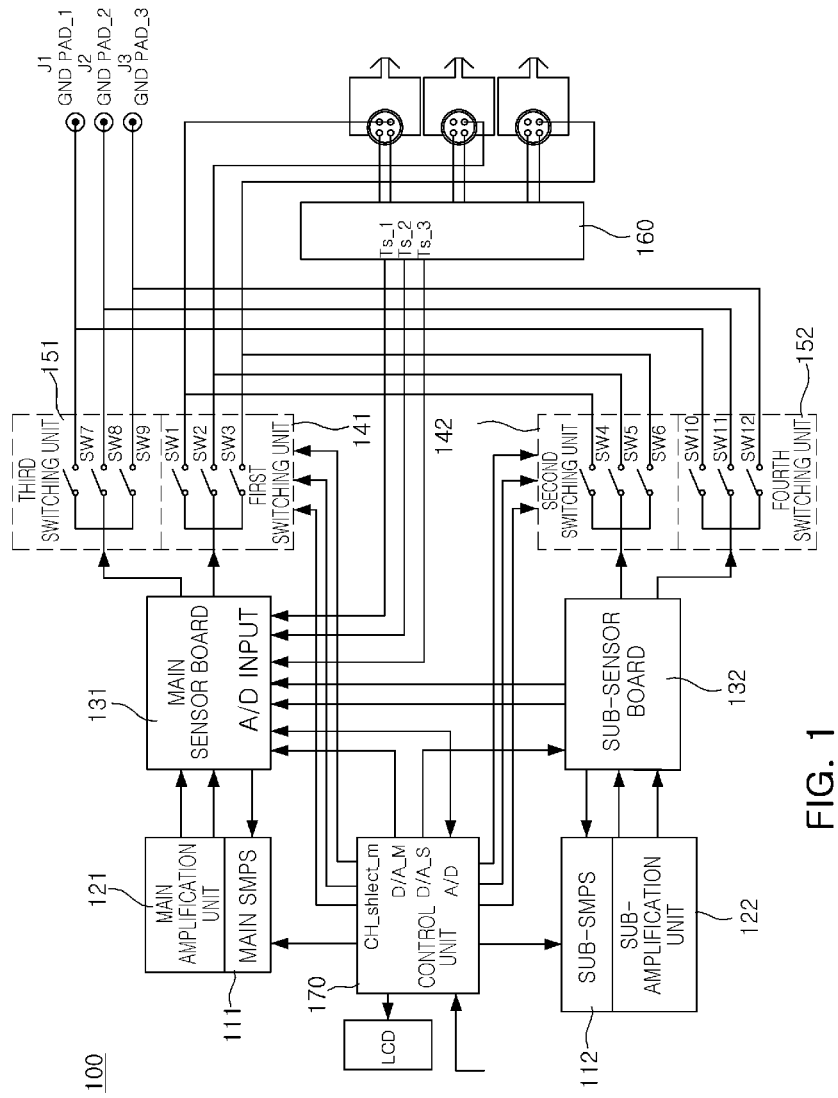
FIG. 1 is a view illustrating a system for ablation utilizing multiple electrodes according to an exemplary embodiment of the present disclosure.

Hereinafter, exemplary embodiments will be described in detail with reference to the accompanying drawings so that they may be apparent to those of ordinary skill in the art. In the following descriptions of the exemplary embodiments, detailed descriptions related to well-known functions or configurations will be ruled out in order not to unnecessarily obscure subject matters of the exemplary embodiments of the present disclosure. In addition, elements having similar functions and performing similar operations may be denoted by the same reference numerals throughout the drawings.

Furthermore, in the present disclosure, when an element is referred to as being "connected to" or "coupled to" another element, it may be directly connected or coupled to the other element or intervening elements may be present. It will be further understood that the terms "comprises" and/or "comprising" used herein specify the presence of stated features or elements, but do not preclude the presence or addition of one or more other features or elements.

FIG. 1 is a view illustrating a system 100 for ablation, utilizing multiple electrodes, according to an exemplary embodiment of the present disclosure.

Referring to FIG. 1, the ablation system 100 of the exemplary embodiment of the present disclosure may include: switching mode power supplies (SMPSs) 111 and 112 supplying power; amplification units 121 and 122 providing radio frequency (RF) power by amplifying power; sensor boards 131 and 132 monitoring current values and voltage values when RF power is applied to tissue through a pair of electrodes previously selected from first to third electrodes; switching units 141 and 142 each transmitting RF power provided by the amplification units 121 and 122 to one of the first to third electrodes; switching units 151 and 152 making connection to or breaking connections with ground pads; a temperature sensing unit 160 measuring temperatures; and a control unit 170 controlling each element of the ablation system 100.

In detail, the SMPSs 111 and 112 include a main SMPS 111 supplying main power and a sub-SMPS 112 supplying sub-power.

The amplification units 121 and 122 include: a main amplification unit 121 providing main RF power by amplifying main power supplied from the main SMPS 111; and a sub-amplification unit 122 providing sub-RF power by amplifying sub-power supplied from the sub-SMPS 112.

The sensor boards 131 and 132 include a main sensor board 131 and a sub-sensor board 132. When main RF power and sub-RF power are applied to a pair of electrodes previously selected from the first to third electrodes, the main sensor board 131 monitors the voltage and current of the main amplification unit 121, and the sub-sensor board 132 monitors the voltage and current of the sub-amplification unit 122.

Specifically, during ablation, the sensor boards 131 and 132 read a high frequency root-mean-square current Irms flowing in tissue and a high frequency root-mean-square voltage Vrms applied between both ends of the tissue and transmit read values to the control unit 170 so that the control unit 170 may calculate impedance.

In addition, the main sensor board 131 may have an analog/digital (A/D) conversion function, and the sub-sensor board 132 may not have an A/D conversion function. In this case, the sub-sensor board 132 may transmit high frequency root-mean-square current and voltage values to the main sensor board 131, and the main sensor board 131 may transmit the values to the control unit 170 after A/D conversion. In addition, the main sensor board 131 converts a temperature value received from the temperature sensing unit 160 from analog to digital and transmits the converted temperature value to the control unit 170.

The switching units 141 and 142 include: a first switching unit 141 transmitting main RF power received from the main amplification unit 121 to one of the first to third electrodes; and a second switching unit 142 transmitting sub-RF power received from the sub-amplification unit 122 to one of the first to third electrodes.

According to a control signal from the control unit 170, the first and second switching units 141 and 142 may apply RF power to a pair of electrodes previously selected from the first to third electrodes. In detail, the first switching unit 141 may transmit main RF power to one of the first to third electrodes, and the second switching unit 142 may transmit sub-RF power to one of the other electrodes.

In detail, the first switching unit 141 includes a first switch SW1 transmitting main RF power to the first electrode, a second switch SW2 transmitting main RF power to the second electrode, and a third switch SW3 transmitting main RF power to the third electrode. After one of the first switch SW1 to third switch SW3 is turned on according to a control signal from the control unit 170, main RF power is transmitted to one of the first to third electrodes through the turned-on switch.

In detail, the second switching unit 142 includes a fourth switch SW4 transmitting sub-RF power to the first electrode, a fifth switch SW5 transmitting sub-RF power to the second electrode, and a sixth switch SW6 transmitting sub-RF power to the third electrode. After one of the fourth switch SW4 to sixth switch SW6 is turned on according to a control signal from the control unit 170, sub-RF power is transmitted through the turned-on switch to one of the first to third electrodes to which main RF power is not transmitted.

The switching units 151 and 152 include: a third switching unit 151 making or breaking the connection between the main amplification unit 121 and a ground pad; and a fourth switching unit 152 making or breaking the connection between the sub-amplification unit 122 and a ground pad.

Each of the third and fourth switching units 151 and 152 includes three switches SW7-SW9 and SW10-SW12 respectively corresponding to the first to third electrodes, and one of the three switches is turned on for connection to a ground pad according to the same control signal as that applied to the first and second switching units 141 and 142.

The temperature sensing unit 160 includes temperature sensor circuits respectively allocated to the first to third electrodes and transmits temperature values measured using the temperature sensor circuits to the main sensor board 131 so that connection states of the first to third electrodes may be checked using the temperature values.

The control unit 170 generates control signals to control operations of elements constituting the ablation system 100.

In detail, the control unit 170 controls the first and second switching units 141 and 142 to apply RF power to a pair of electrodes previously selected from the first to third electrodes. To this end, the control unit 170 stores information related to a pair of electrodes to which main RF power and sub-RF power will be transmitted and outputs a control signal to the first and second switching units 141 and 142 based on the stored information.

For example, the control unit 170 may turn on one pair selected from a pair of the first switch SW1 and fifth switch SW5, a pair of the second switch SW2 and sixth switch SW6, and a pair of the third switch SW3 and fourth switch SW4 according to the stored information related to a pair of electrodes, so as to apply RF power to the pair of electrodes.

In addition, the control unit 170 applies signals D/A_M and D/A_S respectively to the SMPSs 111 and 112 through the sensor boards 131 and 132 so as to determine output values of the SMPSs 111 and 112. D/A_M and D/A_S values are respectively used to determine direct current (DC) output values (for example, ranging from 0 V to 100 V) of the SMPSs 111 and 112, and the DC output values of the SMPSs 111 and 112 are respectively transmitted to the amplification units 121 and 122.

In addition, during ablation, the control unit 170 calculates the impedance of tissue by using a high frequency root-mean-square current value and a high frequency root-mean-square voltage value received from the main sensor board 131. Then, the control unit 170 compares the calculated impedance with a preset reference value for increasing or reducing RF output according to results of the comparison.

In addition, a temperature value measured using the temperature sensing unit 160 is transmitted to the control unit 170 through the main sensor board 131, and if the temperature value is greater than a preset critical value, RF output may be interrupted under the control of the control unit 170. In addition, the control unit 170 may determine whether an electrode is normally connected based on the temperature value and may inform a user of results of the determination.

Figure 2:
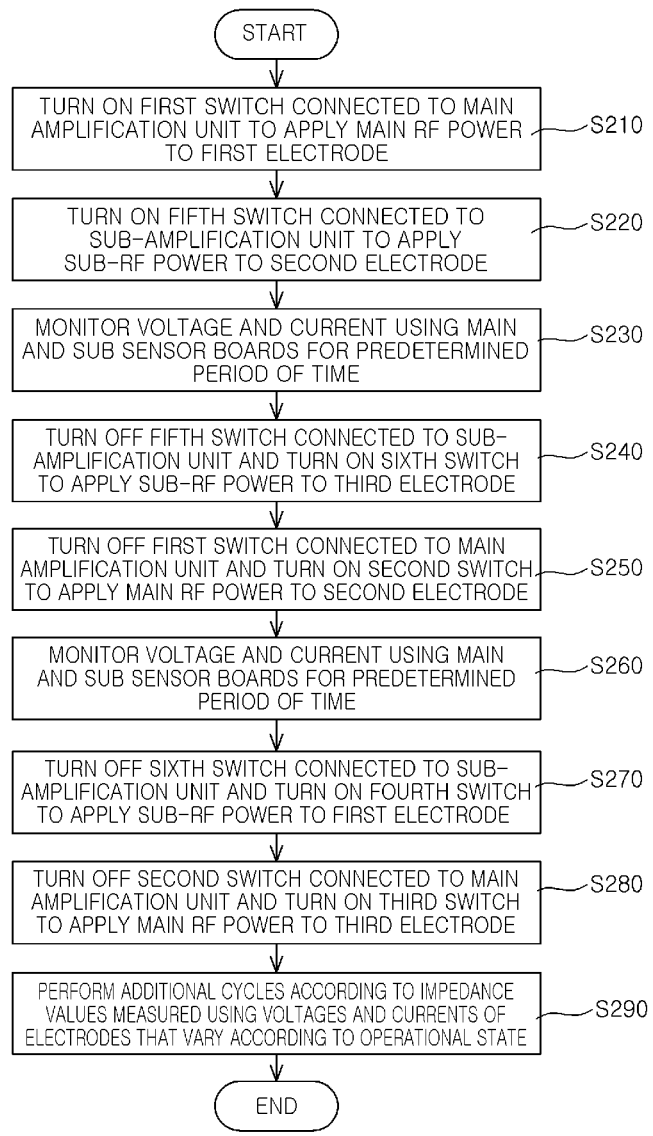
FIG. 2 is a flowchart illustrating a method for controlling a system for ablation utilizing multiple electrodes, according to an exemplary embodiment of the present disclosure.

FIG. 2 is a flowchart illustrating a method for controlling a system for ablation utilizing multiple electrodes, according to an exemplary embodiment of the present disclosure.

Referring to FIG. 2, first, main RF power is applied to a first electrode by turning on a first switch SW1 connected to a main amplification unit (S210), and then sub-RF power is applied to a second electrode by turning on a fifth switch SW5 connected to a sub-amplification unit (S220).

Then, a main sensor board and a sub-sensor board monitor current and voltage values for a predetermined period of time (S230).

Next, the fifth switch SW5 connected to the sub-amplification unit is turned off, and a sixth switch SW6 is turned on to apply sub-RF power to a third electrode (S240). In addition, the first switch SW1 connected to the main amplification unit is turned off, and a second switch SW2 is turned on to apply main RF power to the second electrode (S250).

Then, the main sensor board and the sub-sensor board monitor current and voltage values for a predetermined period of time (S260).

Next, the sixth switch SW6 connected to the sub-amplification unit is turned off, and a fourth switch SW4 is turned on to apply sub-RF power to the first electrode (S270). In addition, the second switch SW2 connected to the main amplification unit is turned off, and a third switch SW3 is turned on to apply main RF power to the third electrode (S280).

Thereafter, additional cycles may be performed according to impedance values measured using voltages and currents of the electrodes which vary according to operational states (S290). For example, the range of impedance increasing as ablation proceeds may be divided into two steps, and output may be decreased according to the step in which a measured impedance value is included. In this case, after cooling tissue by a switching operation for a predetermined period of time, the impedance of the tissue may be measured again to determine whether to perform a second cycle.

According to one or more of the above-described exemplary embodiments of the present disclosure, RF power is sequentially applied to predetermined pairs of electrodes in the ablation system utilizing multiple electrodes so that a time necessary for obtaining a certain ablation size may be decreased. As a result, a time necessary for a doctor to perform an operation on a patient may be decreased. In addition, although an operation is performed on a plurality of parts of the body, the parts of the body may be treated by ablation.

The scope of the present invention is not limited to the above-described exemplary embodiments and the accompanying drawings. It will be apparent to those of ordinary skill in the art that the constituent elements described above in the exemplary embodiments of the present disclosure could be substituted, modified, or varied without departing from the scope of the present invention.

The invention claimed is:

1. A system for ablation, comprising:
a main amplification unit for providing main radio frequency (RF) power by amplifying received power;
a sub-amplification unit for providing sub-RF power by amplifying received power;
a first switching unit for transmitting the main RF power provided by the main amplification unit to one of first to third electrodes;
a second switching unit for transmitting the sub-RF power provided by the sub-amplification unit another one of the first to third electrodes; and
a control unit for controlling the first and second switching units to apply the main RF power and the sub-RF power to a pair of respective electrodes previously selected from the first to third electrodes.

2. The system of claim 1, wherein the first switching unit comprises:
a first switch for transmitting the main RF power to the first electrode;
a second switch for transmitting the main RF power to the second electrode; and
a third switch for transmitting the main RF power to the third electrode,
wherein one of the first to third switches is configured to be turned on according to a control signal transmitted from the control unit so as to transmit the main RF power to one of the first to third electrodes.

3. The system of claim 2, wherein the second switching unit comprises:
a fourth switch for transmitting the sub-RF power to the first electrode;
a fifth switch for transmitting the sub-RF power to the second electrode; and
a sixth switch for transmitting the sub-RF power to the third electrode,
wherein one of the fourth to sixth switches is configured to be turned on according to a control signal transmitted from the control unit so as to transmit the sub-RF power to one of the first to third electrodes to which the main RF power is not transmitted.

4. The system of claim 1, further comprising:
a main sensor board is configured to monitor a voltage and a current of the main amplification unit while the main RF power and the sub-RF power are applied to the pair of respective electrodes previously selected from the first to third electrodes; and
a sub-sensor board is configured to monitor a voltage and a current of the sub-amplification unit while the main RF power and the sub-RF power are applied to the pair of respective electrodes previously selected from the first to third electrodes.

5. The system of claim 4, wherein during ablation, the control unit is configured to calculate a degree of impedance of tissue by using voltage and current values monitored by the main sensor board and the sub-sensor board and is configured to compare the degree of impedance with a preset reference value to increase or decrease the main RF power and the sub-RF power.

6. The system of claim 1, further comprising:
a third switching unit is configured to make or break a connection between the main amplification unit and a ground pad; and
a fourth switching unit is configured to make or break a connection between the sub-amplification unit and the ground pad.

7. The system of claim 1, further comprising a temperature sensing unit comprising temperature sensors respectively allocated to the first to third electrodes and is configured to transmit temperature values measured using the temperature sensors to a main sensor board.

8. The system of claim 7, wherein the control unit is configured to receive the temperature values from the main sensor board and compare the temperature values with a preset critical value, and if one of the temperature values is greater than the preset critical value, the control unit is configured to interrupt the main RF power and the sub-RF power.

9. The system of claim 7, wherein the control unit is configured to make a determination whether the first to third electrodes are normally connected based on the temperature values received from the main sensor board and is configured to inform a user of results of the determination.

* * * * *